US 6,595,204 B2

(12) United States Patent
Genova et al.

(10) Patent No.: US 6,595,204 B2
(45) Date of Patent: Jul. 22, 2003

(54) SPACER FOR AN INHALER

(75) Inventors: Perry A. Genova, Chapel Hill, NC (US); Warren R. Jewett, Cary, NC (US)

(73) Assignee: IEP Pharmaceutical Devices Inc., Raleigh, NC (US)

( * ) Notice: Subject to any disclaimer, the term of this patent is extended or adjusted under 35 U.S.C. 154(b) by 127 days.

(21) Appl. No.: 09/797,468

(22) Filed: Mar. 1, 2001

(65) Prior Publication Data

US 2002/0121276 A1 Sep. 5, 2002

(51) Int. Cl.[7] .............................................. A61M 11/00
(52) U.S. Cl. .............................. 128/200.23; 128/203.12
(58) Field of Search ....................... 128/200.14–200.23, 128/203.12, 203.15, 200.24, 203.23, 204.18, 207.14

(56) References Cited

U.S. PATENT DOCUMENTS

| 3,994,421 | A | | 11/1976 | Hansen |
| 4,292,966 | A | | 10/1981 | Mono et al. |
| 4,534,343 | A | | 8/1985 | Nowacki et al. |
| 4,674,491 | A | | 6/1987 | Brugger et al. |
| 4,796,614 | A | | 1/1989 | Nowacki et al. |
| 4,852,561 | A | | 8/1989 | Sperry |
| 4,926,852 | A | | 5/1990 | Zoltan et al. |
| 5,012,803 | A | | 5/1991 | Foley et al. |
| 5,012,804 | A | | 5/1991 | Foley et al. |
| 5,447,151 | A | * | 9/1995 | Bruna et al. ............ 128/203.15 |
| 5,505,194 | A | | 4/1996 | Adjei et al. |
| 5,904,139 | A | * | 5/1999 | Hauser ................ 128/200.23 |
| 6,039,042 | A | * | 3/2000 | Sladek ................ 128/200.23 |
| 6,202,643 | B1 | * | 3/2001 | Sladek ................ 128/200.23 |
| 6,257,233 | B1 | * | 7/2001 | Burr et al. ............ 128/203.15 |

FOREIGN PATENT DOCUMENTS

| FR | 2 561 106 | | 3/1984 | |
| WO | 01/07107 | * | 2/2001 | ............ 128/200.23 |

OTHER PUBLICATIONS

International Search Report issued by the European Patent Office for corresponding PCT application No. PCT/US02/06215 dated Jul. 2, 2002.

* cited by examiner

Primary Examiner—Glenn K. Dawson
(74) Attorney, Agent, or Firm—Frommer Lawrence & Haug LLP; Ronald R. Santucci

(57) ABSTRACT

A spacer used with aerosol inhalers designed to lower plume force to comfortable levels and to be compact in size in order to conveniently fit in a pocket or purse as part of a drug delivery/actuator system with the geometry and material of the spacer have been selected to provide easy attachment to inhalers, to minimize drug retention, and to provide efficient dose delivery.

16 Claims, 5 Drawing Sheets

SPACER FOR AN INHALER

BACKGROUND OF THE INVENTION

1. Field of the Invention

Figure 1A:
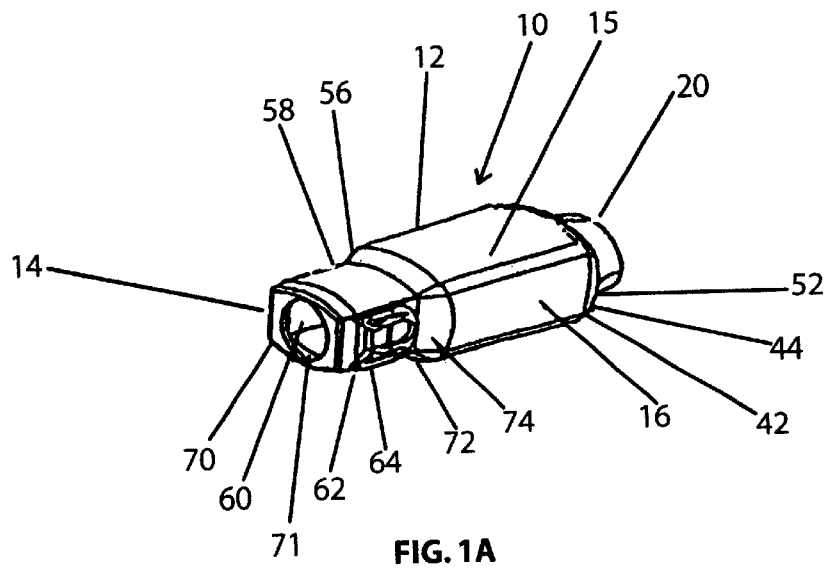
Figure 1B:
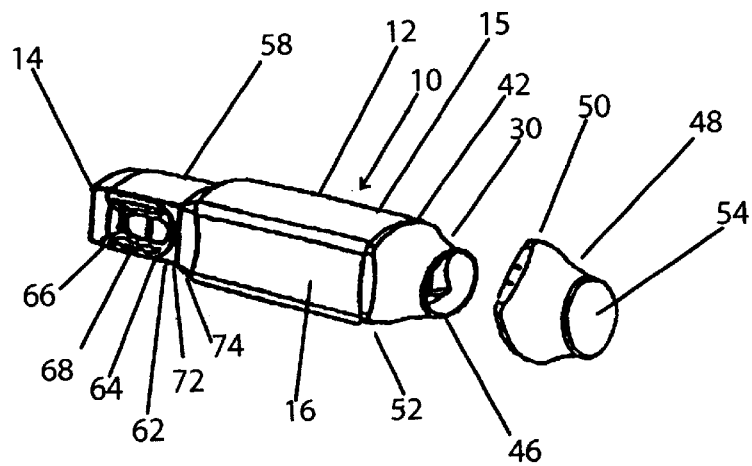
Figure 2:
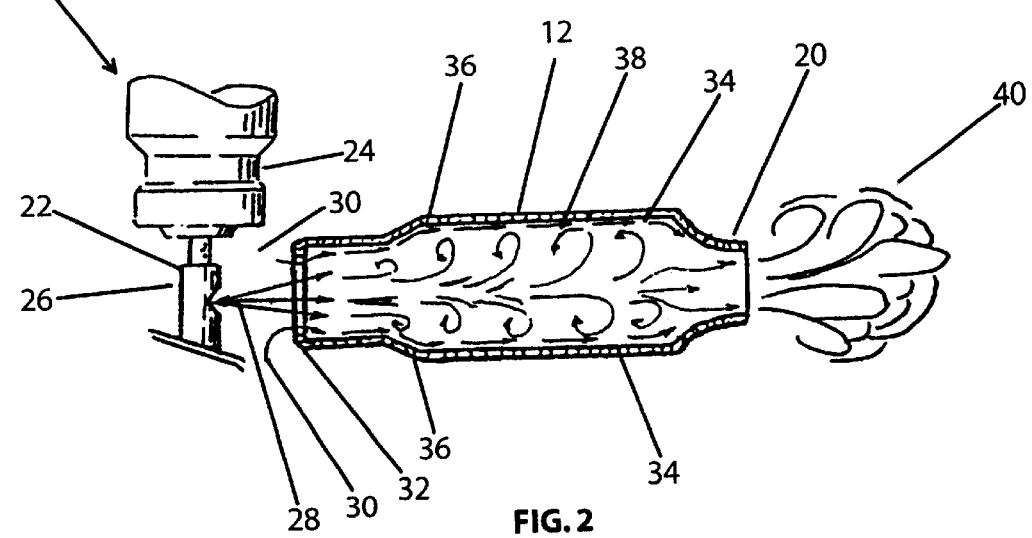

This invention relates to a spacer for use with a breath coordinated inhaler having a connection member for the inhaler providing improved dispensing of medicament, as well as attachment, and stowage with a breath coordinated inhaler. The spacer comprises a longitudinal air chamber shaped to be held in hand and compact enough to be conveniently portable with a breath coordinated inhaler.

2. Description of the Prior Art

In the prior art, it is well known that pressurized metered dose inhalers (pMDIs) can be used to deliver aerosol drugs or other inhalants to a patient. Typically drug from pMDIs exit the spray jet orifice in the form of aerosolized particles at velocities in excess of 50 meters/second. When the aerosol particles reach the back of the throat, the velocity can be 20 meters/second or more.

Conventional pMDIs by the very nature of their drug delivery mode can produce an inconsistency in dose and region of deposition in the lung. Problems can include: a chilling effect of the propellant which may cause patients to cease the necessary inhalation maneuver prior to completion; a high velocity of aerosol which tends to encourage rapid inhalation restricting drug distribution in the lung; and the impact upon the throat of high velocity aerosol frequently causing gagging which can alter or halt the inhalation process.

To minimize these problems and to deliver the drug in a more respirable form, spacers exist that are of numerous physical shapes and designs. Some are as simple and straightforward as extension tubes placing the mouth at a greater distance from the spray. Others decelerate the aerosol by means of tortuous flow path routes or bluff body impact areas. While effective in minimizing the problems of dose delivery by conventional pMDIs, the designs used for existing spacers can contribute to the loss of drug within the spacers.

Another spacer category used to minimize the problems of conventional pMDIs are expansion chambers into which pMDIs are discharged. Medication is presented as a cloud having little or no exit impact force. An advantage is that the patient inhales the cloud created by aerosolizing a solution or suspension or dry powder with no need for concern regarding a synchronized pMDI discharge and inhalation maneuver. Problems arise with dose variability associated with retained drug. The time interval between presenting the aerosol to the chamber and inhalation may be such to cause "Rain Out", i.e. the settling of drug onto the walls of the chamber. "Rain Out" can contribute to the loss of drug.

Also, material selection can cause drug loss. Since spacers must be manufactured from bio-compatible and drug compatible materials, these materials can carry an electrostatic charge. Materials which carry static charge can significantly increase drug retention in actuators and spacers.

As a result of the different design and material types of spacers as well as designs of attachment to inhalers; deposition and retention of the delivered dose of drug can be inconsistent. Because of this inconsistency, all of these devices retain drug, several over 50% requiring dispensing of larger doses to ensure adequate delivery. Since many of the drugs administered by inhalants are very expensive, more efficient delivery is an economic imperative.

Also, with few exceptions all spacers are relatively large. That is, they are not conveniently portable with the inhaler in a pocket or a purse. Those few which are smaller and part of the inhaler actuator are among those retaining the most drug; therefore, more efficient delivery in a compact spacer can be practical as well as economic in use.

Examples of prior art in this field include U.S. Pat. No. 4,534,343 entitled "Metered Dose Inhaler" issued to Nowacki et al. on Aug. 13, 1986; U.S. Pat. No. 4,674,491 entitled "Inhaler" issued to Brugger et al. on Jun. 23, 1987; U.S. Pat. No. 4,796,614 entitled "Collapsible Inhalation Valve" issued to Nowacki et al. on Jan. 10, 1989; U.S. Pat. No. 4,852,561 entitled "Inhalation Device" issued to Sperry on Aug. 1, 1989; U.S. Pat. No. 4,926,852 entitled "Medication Delivery System Phase One" issued to Zoltan et al on May 22, 1990; U.S. Pat. No. 5,012,803 entitled "Modular Medication Inhaler" issued to Foley et al. on May 7, 1991; U.S. Pat. No. 5,012,804 entitled "Medication Inhaler With Adult Mask" issued to Foley et al. on May 7, 1991; U.S. Pat. No. 5,505,194 entitled "Elliptical Cylinder Portions" issued to Adjei et al. on Apr. 19, 1996; and U.S. Pat. No. 5,904,139 entitled "Breath Coordinated Inhaler" issued to Hauser on May 18, 1999.

SUMMARY OF THE INVENTION

It is therefore a further object of the invention to provide a spacer small enough to be incorporated as part of an inhaler actuator.

It is therefore an object of the invention to provide a spacer in which drug delivery is optimized with the use of a breath coordinated inhaler.

It is therefore a still further object of the invention to provide a spacer small enough to be used as an attachable accessory.

It is therefore a still further object of the invention to provide a spacer in which drug retention is minimized.

It is therefore a further object of the invention to provide a spacer which inhibits the velocity of inhalant to the user.

It is therefore a still further object of the invention to provide a spacer with a minimized impact of inhalant delivery to the user.

To attain the objects described the spacer will be molded to have attachment points which will be easily accommodated with the spacer docking piece of the breath coordinated inhaler sometimes referred to herein as "(BCI)" of U.S. Pat. No. 5,904,139, the disclosure of which is incorporated herein by reference. When used with the BCI, the spacer has the advantages of an expansion chamber without the level of drug loss. Uniformity of dose delivery can be better assured as a result of discharge synchronization, with a controlled inspiration rate and delivery of a soft plume via the spacer.

The spacer will be molded with a generally rectangular cross section with slightly curved walls. The ratio of wall height to width of the cross section is at a ratio which optimizes decelerating pMDI discharge. As a result, drug exiting the spacer has a low impact plume force of 1–5 mN and a velocity of less than 1 meter per second. Another advantage of this design is that drug retention is reduced. Combined with the spacer sealing efficiently with a breath coordinated inhaler, both the attributes of drug availability and dose uniformity will be enhanced.

Also, based upon the ratio of wall height to cross section, the spacer can be made small enough to be incorporated as part of an inhaler actuator or to be used as an attachable accessory.

Also, the spacer made of material that has a slight electrical conductivity (1 Megohm or less/cm). This slight electrical conductivity inhibits electrostatic surface effects that would otherwise attract and retain drug. This inhibition can also lead to greater drug availability and dose uniformity.

These and other objects and characteristics of the present invention will become apparent from the further disclosure to be made in the detailed description given below.

BRIEF DESCRIPTION OF THE DRAWINGS

The preferred embodiments of the present invention will now be explained in detail with reference to the accompanying drawings, wherein:

FIGS. 1A and 1B are isometric views of the spacer of the present invention.

FIG. 2 is a cross-sectional view of the spacer of the present invention illustrating a flow pattern when a pressurized multidose inhaler (pMDI) is discharged into the spacer.

FIG. 3 is an exploded assembly view of the spacer of the present invention and the breath coordinated inhaler of U.S. Pat. No. 5,904,139.

FIG. 4 depicts the spacer of the present invention and breath coordinated inhaler in dose delivery mode.

FIG. 5 depicts the attachment and detachment of the spacer of the present invention from the breath coordinated inhaler.

FIG. 6 depicts the storage of the spacer of the present invention on the breath coordinated inhaler.

DETAILED DESCRIPTION OF THE PREFERRED EMBODIMENT

Referring now to the drawings in detail wherein like numerals refer to like elements throughout the several views.

FIGS. 1A and 1B depict a molded spacer 10 made, preferably, of polypropylene, however, any other material suitable for purpose may be used. The polypropylene preferably includes additives of anti-static material. This anti-static material will be sufficiently electrically conductive (Resistivity of 1 Megohm or less/cm) to inhibit retained surface charge thereby reducing deposition of the drug in the spacer. This anti-static material is currently available as Stat Kon. Stat Kon may be obtained from LNP Engineering Plastics, Inc. 475 Creamery Way, Exton, Pa. 19341; (610) 363-4500.

The body 12 of the spacer 10 is an elongated hollow housing. The body 12, exclusive of the inhaler adapter 14, is somewhat rectangular defined by lower and upper cross-sectional walls 15 which are supported by slightly curved (outwardly bowed) side-walls 16. The ratio of the height of each side-wall 16 to the width of each cross-sectional wall 15 is 0.78 or approximately 3 to 4. In general, the cross-sectional width to height ratio of between 1 (a circle) and 0.70 have been found to be efficient in decelerating pMDI aerosol discharge with the least drug retention. The pMDI aerosol discharge can be efficiently decelerated to a velocity of less than 1 meter/second.

The length of the body 12 is, preferably, a minimum of two times the width of a cross-sectional wall 15. The length of the body 12 combined with the contoured geometries of the cross-sectional wall 15 and side-walls 16 enhances aerosol expansion in a decelerated turbulent flow pattern as shown in FIG. 2.

FIG. 2 illustrates a flow pattern within the spacer body 12 when a pressurized multi-dose inhaler (pMDI) 18 is discharged as the patient inhales through the mouthpiece 20. The inhaler 18 is first shaken. The spacer body 12 is rotated down 90 degrees to the use position, slid back to engage the pMDI actuator body 22 and the mouthpiece 20 is inserted into patient's mouth. Upon depressing the pMDI canister 24, drug is discharged via stem block 26 into spacer body 12.

Drug discharged 28 at high velocity enters spacer body 12 where it, along with patient's inhalation, cause ambient air 30 to enter from the inlet end 32 of the inhaler adapter 14. This ambient air 30 becomes entrained along the interior 34 of the spacer body 12 providing a boundary layer 36 throughout transit of the spacer. This boundary layer 36 compresses the flow pattern within the spacer body 12 and limits the deposition and retention of drugs within the spacer body 12. Propellant evaporation and turbulent flow with concomitant deceleration 38 occur as the drug discharged 28 moves toward the mouthpiece 20 to provide a plume 40. There is some minimal exit velocity and a low impact force of 7 mN in the plume 40. Minimal exit velocity is advantageous in decreasing "Rain Out" within the spacer. The low force of the plume 40 decreases impact on the user to a point similar to inhaling a suspended cloud of drug.

FIGS. 1A and 1B detail the shape of the spacer 10. In the spacer 10, the distal end 42 of the body 12 is defined by the ends of cross-sectional walls 15 and side-walls 16. The distal end 42 serves to receive a mouthpiece 20. The mouthpiece 20 is provided with a flared end 44 sized to fit inside the distal end 42 of the body 12. The mouthpiece 20 is hollow from end to end. The mouthpiece 20 tapers from the flared end 44 to an outlet end 46 with a smaller cross-sectional area. The outlet end 46 of the mouthpiece 20 has an elliptical diameter to accommodate the mouth of the patient.

Covering the mouthpiece 20 when the inhaler is not in use is a mouthpiece cap 48. The mouthpiece cap 48 is a hollowed contoured piece. The mouthpiece cap 48 is provided with a flared end 50 sized to cover the proximal end 52 of the mouthpiece 20 exterior of the distal end 42 of the body 12. The mouthpiece cover 48 tapers from the flared end 50 to a solid end 54, maintaining a slightly larger hollowed area than the exterior of the mouthpiece 20. This provides for a conforming fit over the mouthpiece 20. The solid end 54 has a smaller cross-sectional area than the flared end 50 and has an elliptical diameter to cover the outlet end 46 of the mouthpiece 20.

On the opposite end 56 of the spacer 10, the body 12 reduces in cross-sectional area by tapering to accommodate the inhaler adapter 14, an integral part of the body 12. The inhaler adapter 14 is a longitudinally shaped chamber formed to receive a commercially available canister of medication under pressure (18 of FIG. 2) or a breath coordinated inhaler (76 of FIG. 3). In FIG. 1B, the inhaler adapter 14 is somewhat rectangular with a hollowed out center defined by lower and upper cross-sectional walls 58 which are supported by slightly curved (outwardly bowed) side-walls 60 and 62.

Side-walls 60, 62 have an axial protrusion 64 tapering outward from the inhaler adapter 14. The axial protrusion 64 on side-wall 60 is not depicted in FIGS. 1A and 1B but is directly opposite the axial protrusion 64 on sidewall 62. Recesses are located in the upper section 66 and the lower section 68 of the axial protrusion 64 to be attachment points for connection to a breath coordinated inhaler or pMDIs.

The inlet end wall 70 of the inhaler adapter 14 has a circular aperture 71 to accommodate a breath coordinated inhaler as well as conventional inhalers. The outlet end of the inhaler adapter 14 is integral with and boundaried by the tapered end 72 of the truncated cross-sectional area 74.

Figure 3:
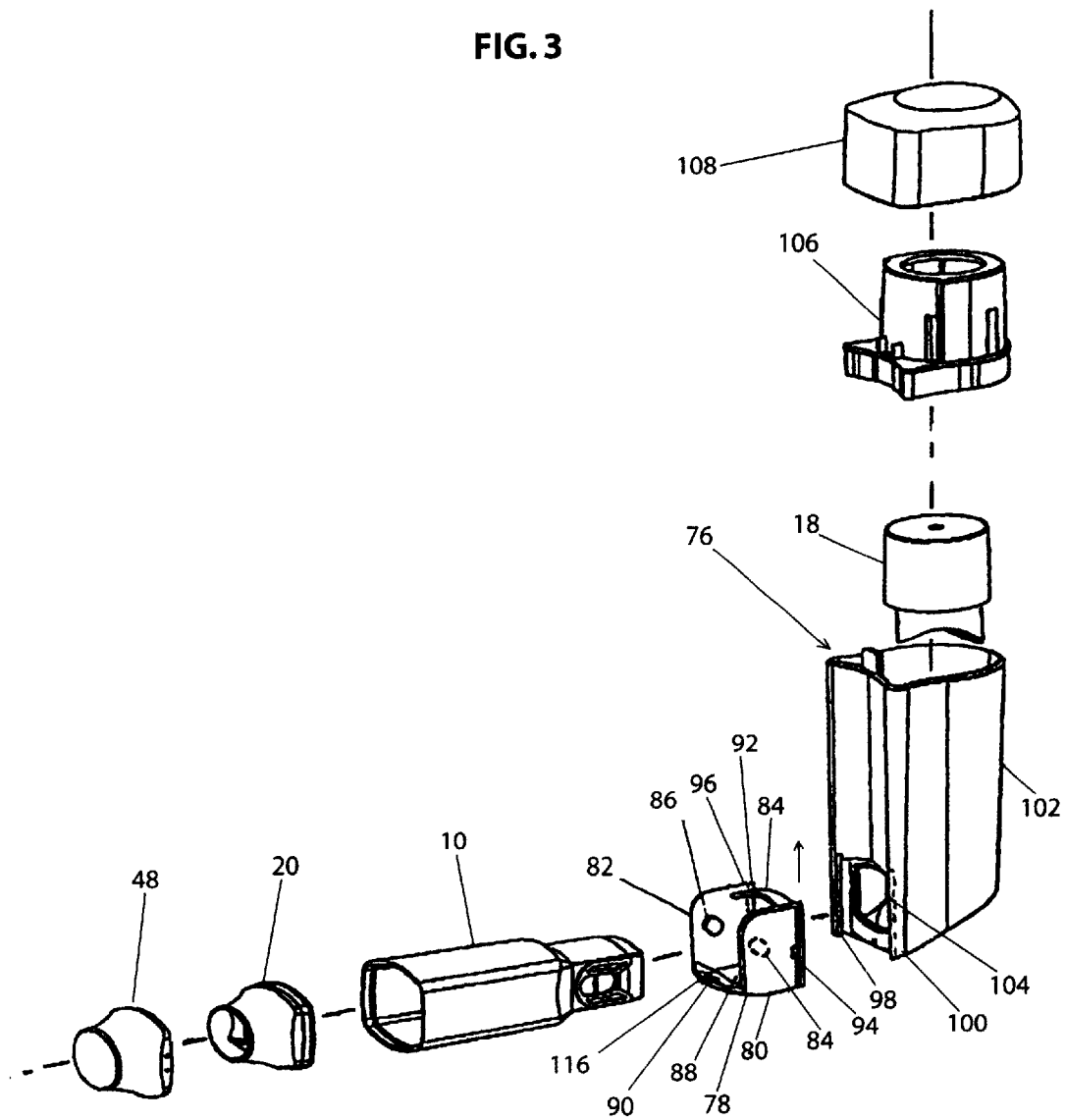

FIG. 3 depicts an exploded assembly view of the mouthpiece cover 48, mouthpiece 20, spacer 10, and breath coordinated inhaler 76. The breath coordinated inhaler depicted is that is shown in U.S. Pat. No. 5,904,139 issued to Hauser. BCI 76 consists of a spacer docking piece 78 detachable from the breath coordinated inhaler 76, to allow for cleaning. The spacer docking piece 78 is a three wall body where the two vertical walls 80, 82 are connected by concave bridge 84. Protruding from the interior of walls 80, 82 are two pivot pins 84, 86. Pivot pins 84, 86 are angled at 135 degrees relative to the bottom 88 of the spacer docking piece 88. The angling of pivot pins 84, 86 assists in the attachment and detachment of spacer 10.

Figure 6:
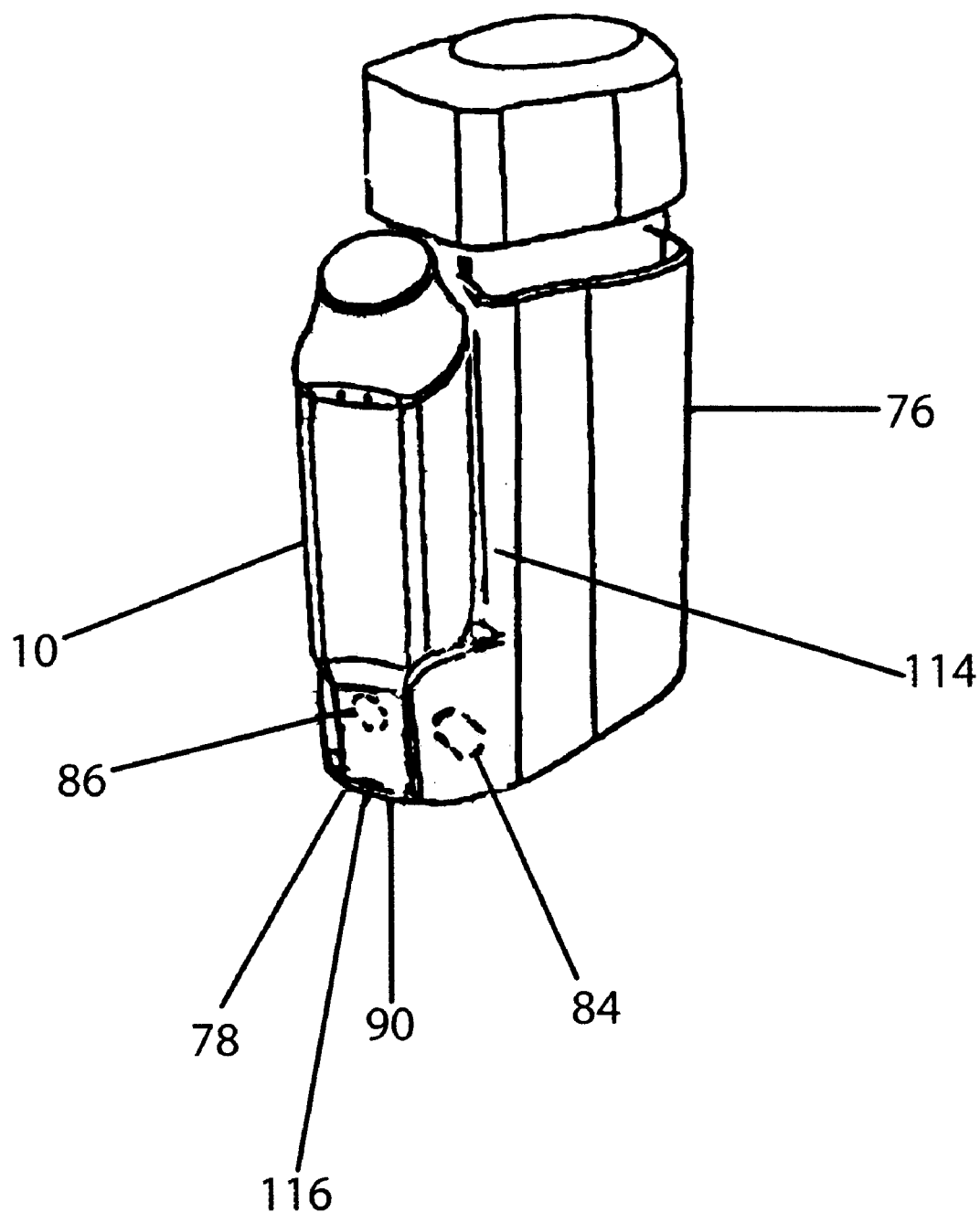

The bottom 88 of the spacer docking piece 78 curves upward to provide a lip 90. The lip 90 provides additional sealing when the spacer 10 is in the stowed position as shown in FIG. 6. In FIG. 3, the distal end 92 of the spacer docking piece 78 has vertical protrusions 94, 96 along the exterior of walls 80, 82. These vertical protrusions 94, 96 are used as securing points with the BCI 76. Protrusions 94, 96 slide into notches 98, 100 which are integral to the lower housing member 102 of the BCI 76.

At the bottom of the lower housing member 102 is an aperture 104. Aperture 104 mirrors the perimeter of the aperture 71 of inlet end wall 70 of the inhaler adapter 14. The close fit of apertures 71 and 104 allows an enhanced seal between the spacer 10 and BCI 76, when the canister 18 is discharged.

Lower housing member 102 is a casing sized to accommodate the dimensional variations of canister 18. The upper housing member 106 slidably fits into the matingly shaped lower housing member 102 and the plunger 108. The upper housing member 106 is a casing sized to accommodate the upper dimensional variations of canister 18 while transmitting pressure applied to the plunger 108 to the cylinder 18. The plunger 108 is a cap in which the interior is sized to accommodate the upper housing member 106 and which the exterior is shaped to accommodate the user.

Figure 4:
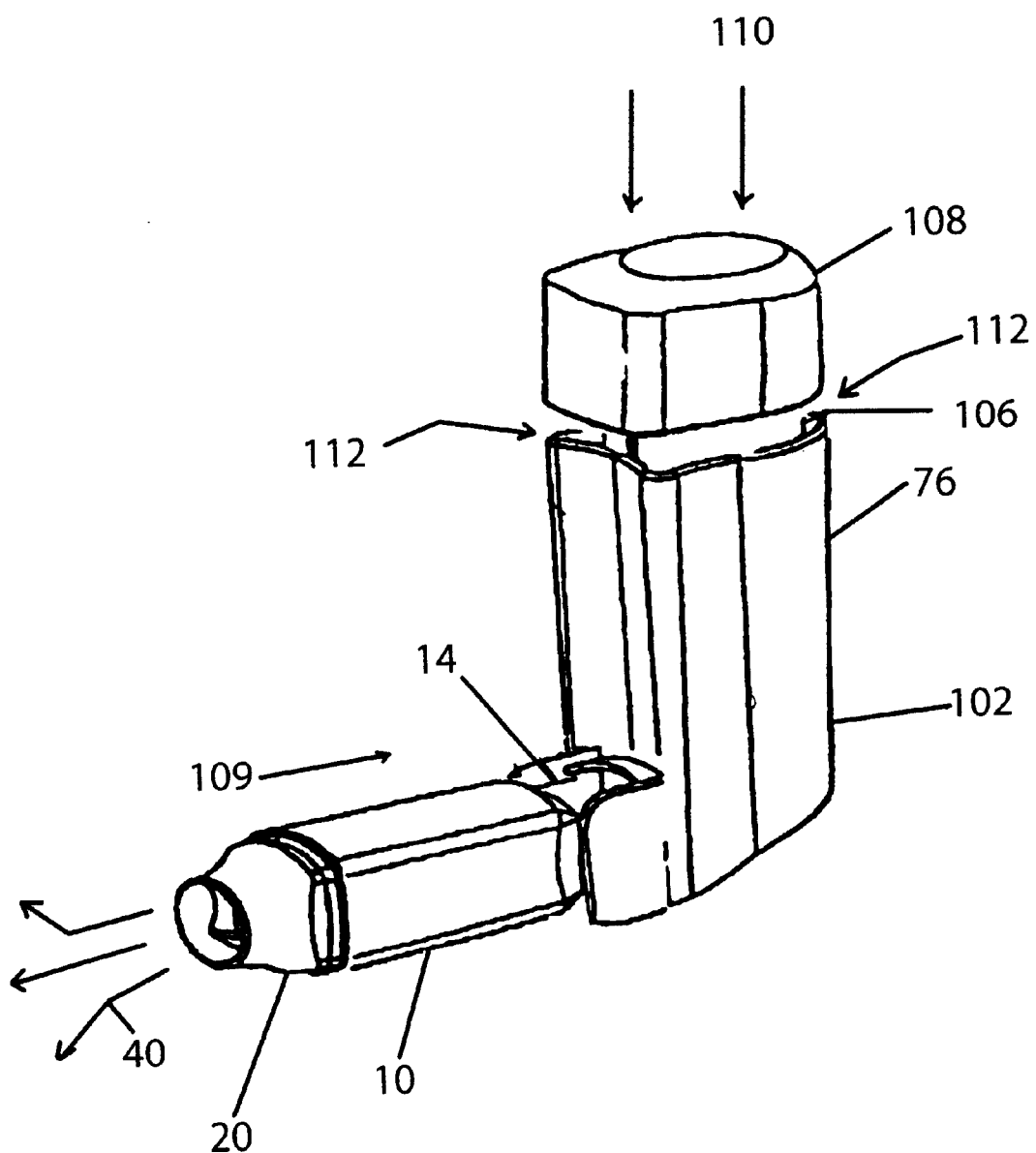

When the spacer 10 is used in conjunction with the breath coordinated inhaler 76, the spacer 10 has the advantages of an expansion chamber without the level of drug loss. In FIG. 4, the spacer 10 and breath coordinated inhaler 76 are attached for dose delivery. The BCI 76 is first shaken. The spacer 10 is set perpendicular to the BCI 76 and is slid back in the direction of arrow 109 in a bayonet fashion to engage the lower housing member 102 of the BCI 76 at the axial protrusion 64 of sidewalls 60, 62 of the inhaler adapter 14. This forms a seal between the spacer 10 and aperture 104 which, in the case of the use of the BCI type device, is important. The mouthpiece 20 is inserted into the user's mouth.

Upon applying pressure 110 to the plunger 108, pressure 110 is transmitted by way of the upper housing member 106 to the cylinder 18 within the BCI 76. Drug is discharged through the aperture 104 of the lower housing member 102 to the aperture 71 of inhaler adapter 14 and into spacer 10. Ambient air 112 enters through spacing between the upper housing member 106 and the plunger 108. Ambient air 112 provides a boundary layer within the spacer 10 assisting in the delivery of the discharged drug. Drug discharged exits the mouthpiece 20 as a plume 40 which the user inhales. Uniformity of dose delivery is better assured as a result of BCI 76 discharge synchronization, with the result being a controlled inspiration rate and delivery of a soft plume 40 of medication via the spacer 10.

Figure 5:
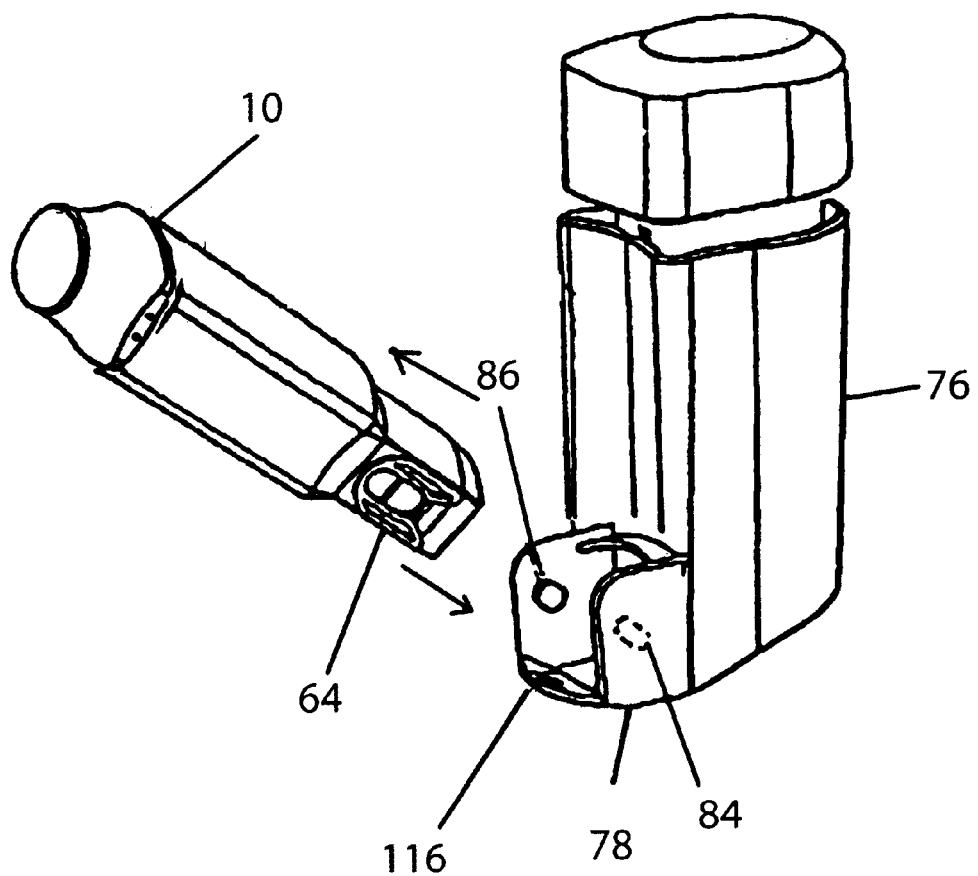

FIG. 5 depicts the attachment and detachment of the spacer 10 from the breath coordinated inhaler 76. The spacer 10 would normally be detached from the BCI 76 for cleaning purposes. A spacer docking piece 78 of the BCI 76 is the mounting point for the spacer 10. The axial protrusion 64 of sidewalls 60, 62 of the inhaler adapter 14 aligns at 45 degrees relative to the BCI 76 and then locks onto the extruding pivot points 84, 86 of the spacer docking piece 78. This process allows easy attachment of the spacer 10 to the BCI 76. The spacer 10 can also detach from the pivot points 84, 86 by sliding out at a 45 degree angle relative to the BCI 76 for cleaning or other purpose.

FIG. 6 shows that the spacer 10 can be rotated ninety degrees upward from its discharge position (shown in FIG. 4) to be stowed within a recessed area 114 of the breath coordinated inhaler 76. The spacer 10 rotates on pivot points 84, 86 to a vertical position with the inhaler adapter 14 resting within the spacer docking piece 76 with a protrusion or nub 116 providing a bearing surface releasibly locking it in place.

While the invention has been described in connection with what is considered to be the most practical and preferred embodiment, it should be understood that this invention is not to be limited to the disclosed embodiment, but on the contrary, is intended to cover various modifications and equivalent arrangements included within the spirit and scope of the appended claims.

What is claimed is:

1. A inhaler for administering aerosol medication, comprising:
    a hollow housing having an opening for dispensing medication;
    an elongated inhaler spacer rotatably coupled with said housing and movable from a first position in which it is parallel with the housing, to a second position which is approximately 90° to said housing, said spacer when in said second position being slidable into an engagement with said opening in said housing.

2. The inhaler of claim 1 further including an inhaler adapter for attachment of said spacer to said housing.

3. The inhaler of claim 2, wherein said spacer is detachable from said housing.

4. The inhaler of claim 2, wherein said spacer includes axial protrusions at an angle of 45 degrees relative to said housing.

5. The inhaler of claim 4, wherein said axial protrusions detach from said housing at an angle of 45 degrees relative to said housing.

6. The inhaler of claim 1, wherein said spacer is stowed in the first position.

7. The inhaler of claim 1, wherein said spacer is releasibly locked in the second position and is in a sealed engagement with the opening in said housing.

8. The inhaler of claim 1, wherein said spacer administers aerosol medication from a pressurized multi-dose inhaler.

9. The inhaler of claim 1, wherein said spacer comprises:
    an elongated hollow spacer housing having a longitudinal axis and two ends located along said longitudinal axis, one end for receiving emissions of a pressurized inhaler with the other end for delivering emissions to a user; and
    wherein the dimensions of said spacer housing are such that the ratio of width to height is in the range of 1 to 0.70 when measured along said longitudinal axis.

10. The inhaler of claim 9, wherein said spacer housing has a length of approximately two times the width of said housing.

11. The inhaler of claim 9, wherein said length is greater than two times the width of said spacer housing.

12. The inhaler of claim 9, further including a mouthpiece.

13. The inhaler of claim 1, wherein said spacer is made of anti-static material.

14. The inhaler of claim 13, wherein said anti-static material has an electrical resistivity of approximately 1 Megaohm/cm or less.

15. The inhaler of claim 1, wherein said spacer administers aerosol medication from a breath coordinated inhaler.

16. The inhaler of claim 9, herein said spacer administers aerosol medication from a pressurized multi-dose inhaler.

* * * * *